(12) United States Patent
Rosenberg et al.

(10) Patent No.: US 6,579,544 B1
(45) Date of Patent: Jun. 17, 2003

(54) METHOD FOR SUPPLEMENTING THE DIET

(75) Inventors: Thomas D. Rosenberg, Salt Lake City, UT (US); Kathleen Deffner, Taylorsville, UT (US)

(73) Assignee: Nutriex, L.L.C., Salt Lake City, UT (US)

( * ) Notice: Subject to any disclaimer, the term of this patent is extended or adjusted under 35 U.S.C. 154(b) by 0 days.

(21) Appl. No.: 09/584,647

(22) Filed: May 31, 2000

(51) Int. Cl.$^7$ ................................................ A61K 35/78
(52) U.S. Cl. ........................ 424/736; 424/682; 424/655; 424/768; 424/94.1; 514/474; 514/458; 514/62; 514/725; 514/276
(58) Field of Search ................................ 424/736, 682, 424/655, 768, 94.1; 514/474, 458, 62, 725, 276

(56) References Cited

U.S. PATENT DOCUMENTS

| | | |
|---|---|---|
| 4,108,849 A | 8/1978 | Thomas |
| 4,929,722 A | 5/1990 | Partain, III et al. |
| 4,946,870 A | 8/1990 | Partain, III et al. |
| 5,053,222 A | 10/1991 | Takasu et al. |
| 5,364,845 A | 11/1994 | Henderson |
| 5,446,070 A | 8/1995 | Mantelle |
| 5,560,928 A * | 10/1996 | DeFelice |
| 5,587,363 A | 12/1996 | Henderson |
| 5,622,693 A | 4/1997 | Funatsu |
| 5,656,286 A | 8/1997 | Miranda et al. |
| 5,719,197 A | 2/1998 | Kanios et al. |
| 5,804,594 A | 9/1998 | Murad |
| 5,849,336 A | 12/1998 | Aoyagi et al. |
| 5,885,829 A | 3/1999 | Mooney et al. |
| 5,895,652 A * | 4/1999 | Giampapa |

OTHER PUBLICATIONS

Snook; Nutrition: a guide to decision making; (1984), Prentice–Hall Inc. New Jersey, pp. 24–25; 374–376.*

* cited by examiner

Primary Examiner—Leon B. Lankford, Jr.
Assistant Examiner—Susan D. Coe
(74) Attorney, Agent, or Firm—Clayton, Howarth & Cannon, P.C.

(57) ABSTRACT

A dietary supplement blend composition is disclosed, the basic formulation of the composition containing vitamins, minerals, and carotenoids. The composition can also contain bioflavonoids, cartilage protectors such as glucosamine or chondroitin, α-lipoic acid, coenzyme Q10, and a source of omega-3 fatty acids such as flax seed oil. The composition is beneficial for improving health and preventing disease, particularly for degenerative conditions. A method for supplementing the diet is also disclosed, wherein the quantity of daily rations of the dietary supplement blend composition is determined based on the person's age, body weight, and quality of diet.

19 Claims, No Drawings

METHOD FOR SUPPLEMENTING THE DIET

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. The Field of the Invention

This invention relates to dietary supplements. More particularly, the invention relates to compositions and methods for supplementing the diet for improving health and preventing disease.

2. Description of Related Art

In advanced countries as high as 90% of serious diseases are degenerative, that is, slowly progressive processes that eventually lead to system failure. Such degenerative conditions may not be recognized until failure occurs, such as compression fracture of a vertebra (osteoporosis), joint pain and limping (osteoarthritis), chest pain and heart attack (arteriosclerosis), blood-tinged stool and bowel obstruction (advanced cancer of the colon). Examples of diseases that are degenerative in their development include adult-onset diabetes, Alzheimer's disease, arteriosclerotic heart attack, arteriosclerotic stroke, diverticulitis, gall bladder disease, hypertension, increased susceptibility to infections, many types of cancer, osteoarthritis, osteoporosis, and vision loss by macular degeneration. Many of these degenerative processes that eventually lead to obvious disease can be prevented by early implementation of optimal nutrition, daily exercise, and achieving an ideal body weight.

U.S. Pat. No. 5,804,594 to Murad describes orally administered pharmaceutical compositions and methods for improving wrinkles and other skin conditions. The composition comprises a sugar compound that is converted to a glycosaminoglycan (GAG) in the patient, such as an N-acetylglucosamine compound or salt or ester thereof; an antioxidant, such as ascorbic acid or a salt or ester thereof; at least one amino acid, such as proline, lysine, cysteine, or methionine; at least one transition metal, such as zinc, manganese, or copper; and a catechin-based component, such as a proanthanol or proanthocyanidin. In addition, the composition can further contain glucosamine, chondroitin, vitamins (such as vitamin E, niacinamide, pyridoxal 5 phosphate-Co B6, and vitamin A), and quercitin.

U.S. Pat. No. 5,364,845 and U.S. Pat. No. 5,587,363 to Henderson disclose a composition for treatment and repair of connective tissue in animals and humans comprising an aminosugar, specifically glucosamine, glucosamine salts, or mixtures thereof, in combination with a GAG, specifically chondroitin, chondroitin salts, or mixtures thereof. This composition can further contain manganese and ascorbate.

U.S. Pat. No. 5,292,538 to Paul & Ashmead discloses a dietary supplement that provides for sustained energy and nutrition for supporting an anabolic physiological state. This composition comprises a blend of simple sugars and more complex carbohydrates, partially hydrolyzed protein, and magnesium in the form of an amino acid chelate. Other ingredients can include lipids, bioavailable minerals in the form of amino acid chelates, anabolic nutrients, vitamins, antioxidants, and lipotropic agents.

U.S. Pat. No. 5,270,297 to Paul & Ashmead discloses a dietary supplement that provides for rehydration and endurance in persons having symptoms of physiological stress. The composition includes a blend of simple sugars, more complex carbohydrates, and magnesium in the form of an amino acid chelate. Other ingredients can include anabolic nutrients, vitamins, electrolyte ions, and other minerals.

While prior art formulas as dietary supplements containing vitamins, minerals, aminosugars, antioxidants, bioflavonoids, and the like are known and are generally suitable for their limited purposes, they possess certain inherent deficiencies that detract from their overall utility in improving health and preventing disease, especially degenerative diseases. For example, the dietary supplement of Murad contains selected vitamins and minerals, but fails to include calcium, which is the mineral most deficient in the diet in the United States, and carotenoids, which are useful in preventing certain cancers, macular degeneration and cataracts, and heart disease. By way of further example, the anabolic composition of Paul & Ashmead contains a wide variety of vitamins and minerals, but is deficient in carotenoids, bioflavonoids, cartilage protectors, omega-3 fatty acids, and coenzyme Q10, all of which are useful in reducing the incidence of degenerative diseases.

In view of the foregoing, it will be appreciated that providing a dietary supplement that contains vitamins, minerals, carotenoids, and also preferably bioflavonoids, omega-3 fatty acids, cartilage protectors, and other nutrients that promote health and reduce degenerative diseases would be a significant advancement in the art.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY AND OBJECTS OF THE INVENTION

It is an object of the present invention to provide a dietary supplement that promotes good health and prevents disease, especially degenerative diseases such as adult-onset diabetes, arteriosclerotic heart attack, arteriosclerotic stroke, hypertension, increased susceptibility to infections, many types of cancer, osteoarthritis, osteoporosis, and vision loss by macular degeneration.

It is another object of the invention to provide a dietary supplement that contains a wide variety of vitamins, minerals, carotenoids and other antioxidants, and cartilage building blocks.

It is a further object of the invention to provide a dietary supplement that contains glucosamine and chondroitin for assisting in building healthy cartilage.

It is still another object of the invention to provide a dietary supplement that contains, in addition to a wide variety of vitamins, minerals, and carotenoids, one or more bioflavonoids, cartilage protectors, sources of omega-3 fatty acids, other scientifically validated antioxidants, and the like.

It is yet another object of the invention to provide a method for providing supplementation of nutrients in the diet by taking into account the age, body weight, and quality of diet of the person to receive the dietary supplement.

These and other objects can be addressed by providing a dietary supplement blend composition comprising:

(a) about 500 to 3,000×(10$^{-3}$) parts by weight of vitamin C;

(b) about 200 to 800 international units of vitamin E;

(c) about 500 to 2,000×(10$^{-3}$) parts by weight of calcium; and (d) an effective amount of a carotenoid.

The effective amount of the carotenoid is preferably about 10 to 300×(10$^{-3}$) parts by weight. Preferably, the carotenoid is a member selected from the group consisting of α-carotene, β-carotene, cryptoxanthin, lutein, lycopene, zeaxanthin, and mixtures thereof, and more preferably is cryptoxanthin, lutein, lycopene, zeaxanthin, or mixtures thereof. In another preferred embodiment of the invention, the composition further comprises about 30 to 1,500×(10$^{-3}$) parts by weight of a bioflavonoid selected from the group consisting of citrus bioflavonoids, grape seed extract, quercetin, rutin, soybean isoflavones, and mixtures thereof. In still another preferred embodiment of the invention, the composition further comprises about 250 to 3,500×(10$^{-3}$) parts by weight of a cartilage protector selected from the group consisting of glucosamine, chondroitin, and mixtures thereof. Yet another preferred embodiment of the invention further comprises a fat soluble vitamin selected from the group consisting of about 1,000 to 20,000 international units of vitamin A; about 50 to 1,000 international units of vitamin D; about 20–400×(10$^{-6}$) parts by weight of vitamin K; and mixtures thereof. Another preferred embodiment of the invention further comprises a water soluble vitamin selected from the group consisting of about 1 to 100×(10$^{-3}$) parts by weight of thiamine; about 1 to 100×(10$^{-3}$) parts by weight of riboflavin; about 0.5 to 50×(10$^{-3}$) parts by weight of niacin; about 1 to 100×(10$^{-3}$) parts by weight of pyridoxine; about 50 to 5,000×(10$^{-6}$) parts by weight of folic acid; about 2 to 200×(10$^{-6}$) parts by weight of vitamin B-12; about 50 to 5,000×(10$^{-6}$) parts by weight of biotin; about 2 to 200×(10$^{-3}$) parts by weight of pantothenic acid; and mixtures thereof. Still another preferred embodiment of the invention further comprises about 50 to 1,000×(10$^{-3}$) parts by weight of magnesium. Another preferred embodiment of the invention further comprises a trace element selected from the group consisting of about 10 to 500×(10$^{-6}$) parts by weight of chromium; about 1 to 10×(10$^{-3}$) parts by weight of copper; about 10 to 500×(10$^{-6}$) parts by weight of iodine; about 2 to 20×(10$^{-3}$) parts by weight of iron; about 1 to 100×(10$^{-3}$) parts by weight of manganese; about 5 to 500×(10$^{-6}$) parts by weight of molybdenum; about 20 to 1,000×(10$^{-6}$) parts by weight of selenium; about 2 to 200× (10$^{-3}$) parts by weight of zinc; about 0.1 to 10×(10$^{-3}$) parts by weight of boron; about 1 to 100×(10$^{-6}$) parts by weight of vanadium; and mixtures thereof. Preferably, the invention further comprises about 50 to 2,000×(10$^{-3}$) parts by weight of flax seed oil or another source of omega-3 fatty acid. Moreover, another preferred embodiment of the invention further comprises a member selected from the group consisting of about 5 to 500×(10$^{-3}$) parts by weight of α-lipoic acid; about 1 to 100×(10$^{-3}$) parts by weight of coenzyme Q10; and mixtures thereof.

A method for supplementing a person's diet comprises:

(a) determining the person's age, body weight, and quality of diet;

(b) determining a quantity of daily rations of a dietary supplement blend composition to be administered to the person based on the person's age, body weight, and quality of diet from the table:

Daily Rations[1] of Dietary Supplement Blend Composition

| Age | Body weight | Excellent Diet | Good Diet | Fair Diet |
|---|---|---|---|---|
| <60 years | <54.5 kg (<120 lbs.) | 4 | 5 | 6 |
|  | 54.5 to 90.9 kg (120 to 200 lbs.) | 5 | 6 | 7 |
|  | >90.9 kg (>200 lbs.) | 6 | 7 | 8 |
| ≧60 years | <54.5 kg (<120 lbs.) | 5 | 6 | 7 |
|  | 54.5 to 90.9 kg (120 to 200 lbs.) | 6 | 7 | 8 |
|  | >90.9 kg (>200 lbs.) | 7 | 8 | 9 |

[1]Although the entire quantity of daily rations may be administered all at once, it is recommended that the rations instead be spread out in administrations of two to three times per day. For example, if the recommended quantity of daily rations is six, three administrations of two rations, spread throughout the day, is preferred.

wherein the dietary supplement blend composition comprises:

(1) about 500 to 3,000×(10$^{-3}$) parts by weight of vitamin C;

(2) about 200 to 800 international units of vitamin E;

(3) about 500 to 2,000×(10$^{-3}$) parts by weight of calcium; and (4) an effective amount of a carotenoid.

(c) administering the quantity of daily rations of the dietary supplement blend composition to the person as determined from the person's age, body weight, and quality of diet.

It is preferable that one (1) ration of the dietary supplement blend, in accordance with the principles of the present invention, reside within one (1) capsule. Of course, any suitable administration vehicle, other than a capsule, may also be used.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

DETAILED DESCRIPTION OF THE INVENTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present compositions and methods for supplementing the diet for improving health and preventing disease are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a dietary supplement containing "a glycosaminoglycan" includes a mixture of two or more of such glycosaminoglycans, reference to "an aminosugar" includes reference to one or more of such aminosugars, and reference to "a carotenoid" includes references to two or more of such carotenoids.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "effective amount" means an amount of a component of the dietary supplement that is nontoxic but sufficient to provide the desired effect and performance at a reasonable benefit/risk ratio attending any dietary supplement. For example, an effective amount of a vitamin or mineral is an amount sufficient to prevent a deficiency thereof and may reduce the incidence of some cancers, i.e., lung (vitamin E, folic acid, vitamin D, selenium), prostate (vitamin E, vitamin D, selenium, lycopene and soybean isoflavones), stomach (vitamin C), colorectal (folic acid, vitamin D, selenium), skin (selenium), cervix (folic acid), and breast (vitamin D); osteoporosis (vitamin D, vitamin K, calcium, magnesium, vanadium, and possibly boron and copper); osteoarthritis (calcium); macular degeneration or cataracts (riboflavin, vitamin C, vitamin E, selenium); heart disease (vitamin E, folic acid, pyridoxine, vitamin A, magnesium, selenium, copper); neurologic disease (thiamine, niacin, pantothenic acid, folic acid, vitamin B-12); or to aid in regeneration of connective tissue (vitamin C, copper, iron, manganese, zinc, glucosamine and chondroitin). An effective amount of a carotenoid is an amount sufficient to reduce the incidence of some cancers, i.e., skin and mucous membranes ($\beta$-carotene), digestive tract ($\beta$-carotene, lycopene), prostate and stomach (lycopene), cervix(cryptoxanthin, $\alpha$-carotene), lung (lutein, $\alpha$-carotene, zeaxanthin); macular degeneration (lutein, zeaxanthin); or heart disease (lycopene). An effective amount of a bioflavonoid is an amount sufficient to decrease the incidence of some cancers, i.e., breast (quercetin, soybean isoflavones), stomach, pancreas, and lung (quercetin), prostate and endometrium (soybean isoflavones); osteoporosis (soybean isoflavones); or heart disease (quercetin, citrus bioflavonoids, grape seed extract, soybean isoflavones). An effective amount of an omega-3 fatty acids source is an amount sufficient to reduce the incidence of some cancers, i.e., breast, colon, and prostate (flax seed oil); or heart disease (flax seed oil). An effective amount of a cartilage protector is an amount sufficient to reduce the incidence of, or relieve the symptoms of, osteoarthritis (glucosamine, chondroitin). An effective amount of $\alpha$-lipoic acid is an amount sufficient to reduce the incidence of cataracts or neurologic disease. An effective amount of coenzyme Q10 is an amount sufficient to reduce the incidence of some cancers or heart disease. Such effective amounts can be determined without undue experimentation by those skilled in the art.

As used herein, "glucosamine" means glucosamine, salts thereof such as glucosamine sulfate or glucosamine succinate, derivatives thereof such as N-acetylglucosamine, and mixtures thereof.

As used herein, "chondroitin" means chondroitin, salts thereof such as chondroitin sulfate, esters thereof, and mixtures thereof.

As used herein, "cartilage protector" means a precursor in the synthesis of cartilage, such as glucosamine or chondroitin.

As used herein, "excellent diet" means an average daily intake of at least 8 servings of vegetables and/or fruits, and at least some intake of a calcium source, and preferably the consumption of animal fats is minimized. It is more preferable, but not required, that an excellent diet also include an average daily intake of at least 1 serving of a calcium source, and at least 3 servings of unrefined grains.

As used herein, "good diet" means an average daily intake of at least 5 servings of vegetables and/or fruits, and preferably the consumption of animal fats is partially managed (i.e. animal fats not commonly eaten but consumption thereof not minimized either). It is more preferable, but not required, that a good diet also include an average daily intake of at least 1 serving of unrefined grains.

As used herein, "fair diet" means an average daily intake of fewer than 5 servings of vegetables and/or fruits, and preferably in which animal fats are commonly eaten.

As used herein, "serving" means an amount of a food defined as follows:

Fruit: One serving of fruit, as referred to herein, shall constitute at least:

½ cup fruit (either whole, chopped, cooked or canned); or

A quantity of dried fruit that would constitute ½ cup in its pre-dried state; or ¾ cup fruit juice.

Vegetables: One serving of vegetables, as referred to herein, shall constitute at least:

1 cup leafy vegetables; or

½ cup non-leafy vegetables, cooked or chopped raw; or

¾ cup vegetable juice.

Unrefined Grains: One serving of unrefined grains, as referred to herein, shall constitute at least:

23 g (0.8 ounces) of bread; or 1 ounce of ready-to-eat cereal; or

½ cup cooked cereal, cooked rice, or cooked pasta.

Calcium: As used herein, "calcium source" means any source of calcium, such as milk, yogurt, cheese or any suitable source. Examples of one serving of a calcium source include, but are not limited to, at least:

1 cup milk or 1 cup yogurt; or 42.6 g (1.5 ounces) of natural cheese; or 58.8 g (2 ounces) of process cheese.

In its most basic form, the dietary supplement blend composition according to the present invention comprises about 500 to $3,000 \times (10^{-3})$ parts by weight of vitamin C, about 200 to 800 international units of vitamin E, about 500 to $2,000 \times (10^{-3})$ parts by weight of calcium, and an effective amount of a carotenoid. A preferred amount of the carotenoid is about 10 to $300 \times (10^{-3})$ parts by weight. Preferably, the carotenoid is a member selected from the group consisting of α-carotene, β-carotene, cryptoxanthin, lutein, lycopene, zeaxanthin, and mixtures thereof, and more preferably is cryptoxanthin, lutein, lycopene, zeaxanthin, or mixtures thereof.

It is also preferable that the composition contain one or more additional ingredients, such as fat soluble vitamins, water soluble vitamins, magnesium, trace elements, bioflavonoids, omega-3 fatty acid sources, cartilage protectors, and other nutrients, such as α-lipoic acid or coenzyme Q10. These nutrients will now be described in more detail.

Vitamins

Vitamins are organic compounds that are required for the normal growth and maintenance of life of animals, including man, who are generally unable to synthesize these compounds by anabolic processes that are independent of environment other than air, and which compounds are effective in small amounts, do not furnish energy, and are not utilized as building units for the structure of the organism, but are essential for the transformation of energy and for the regulation of the metabolism of structural units. Vitamins or their precursors are found in plants, and thus plant tissues are the sources for the animal kingdom of these protective nutritional factors. In addition to carbohydrates, fats, proteins, mineral salts, and water, it is essential that the food of man and animals contain small amounts of these vitamins. If any one of at least 13 of these compounds is lacking in the diet, a breakdown of the normal metabolic processes occurs, which results in a reduced rate or complete lack of growth in children and in symptoms of malnutrition that are classified as deficiency diseases.

The functions of vitamins generally fall into two categories, the maintenance of normal structure and the maintenance of normal metabolic functions. For example, vitamin A is essential for the maintenance of normal epithelial tissue, and vitamin D functions in the absorption of normal bone salts for the formation and growth of a sound bony structure. Certain vitamins, such as thiamine, riboflavin, pantothenic acid, and niacin, are known to be essential constituents of the respiratory enzymes that are required in the utilization of energy from oxidative catabolism of sugars and fats.

It is convenient to divide vitamins into two groups, the water-soluble vitamins and the fat-soluble vitamins. The water-soluble vitamins include ascorbic acid and the B group of vitamins, which consists of some 10 or more well-defined compounds. The fat-soluble vitamins include vitamins A, D, E, and K, since they can be extracted with organic solvents and are found in the fat fractions of animal tissues. For brief reviews of vitamins in general and specific vitamins, see Remington's Pharmaceutical Sciences.

Fat-soluble vitamins. Vitamin A is essential for the maintenance of normal tissue structure and for other important physiologic functions such as vision and reproduction. The source of most of the vitamin A in animals is the carotenoid pigments, i.e. the yellow-colored compounds in all chlorophyll-containing plants. At least 10 different carotenoids exhibit provitamin A activity. For example, α- and β-carotene and cryptoxanthin (found in yellow corn) are important in animal nutrition, β-carotene being the most important. Theoretically, one molecule of β-carotene should yield two molecules of vitamin A. The availability of carotene in foods as sources of vitamin A for humans, however, is low and extremely variable. The conversion of the provitamin to vitamin A occurs primarily in the walls of the small intestine and perhaps to a lesser degree in the liver. Like vitamin A, the carotenes are soluble in organic solvents.

Of the known functions of vitamin A in the body, its role in vision is established best. The retina of man contains two distinct photoreceptor systems. The rods, which are the structural components of one system, are especially sensitive to light of low intensity. A specific vitamin A aldehyde is essential for the formation of rhodopsin, the high molecular weight glycoprotein part of the visual pigment within the rods, and the normal functioning of the retina. By virtue of this relation in the visual process, vitamin A alcohol has been named retinol, and the aldehyde form is named retinal. A vitamin-A deficient person has impaired dark adaptation ("night-blindness").

Vitamin A also aids in the differentiation of cells of the skin (lining the outside of the body) and mucous membranes (linings inside of the body); helps the body fight off infection and sustain the immune system; and, supports growth and remodeling of bone. In addition, dietary vitamin A, in the form of its precursor β-carotene (an antioxidant), may help reduce risk for certain cancers.

Vitamin D is the vitamin effective in promoting calcification of the bony structures of man and animals. It is sometimes known as the "sunshine" vitamin because it is formed by the action of the sun's ultraviolet rays on precursor sterols in the skin. Vitamin D aids in the absorption of calcium from the intestinal tract and the resorption of phosphate in the renal tubule. Vitamin D is necessary for normal growth in children, probably having a direct effect on the osteoblast cells, which influence calcification of cartilage in the growing areas of the bone. A deficiency of vitamin D leads to inadequate absorption of calcium from the intestinal tract and retention of phosphorus in the kidney and thus to faulty mineralization of bone structures. Vitamin D also maintains a stable nervous system and normal heart action.

Vitamin E is a group of compounds (tocol and tocotrienol derivatives) that exhibit qualitatively the biological activity of α-tocopherol. Biological activity associated with the vitamin nature of the group is exhibited by four major compounds: α-, β-, γ-, and δ-tocopherol, each of which can exist in various stereoisomeric forms. The tocopherols act as antioxidants, δ-tocopherol having the greatest antioxidant power. The most critical function of vitamin E occurs in the membranous parts of the cells. Vitamin E interdigitates with phospholipids, cholesterol, and triglycerides, the three main structural elements of the membranes. Since vitamin E is an antioxidant, a favored reaction is with the very reactive and highly destructive compounds called free radicals. Free radicals are products of oxidative deterioration of such substances as polyunsaturated fat. Vitamin E converts the free radical into a less reactive and nonharmful form. Vitamin E also supplies oxygen to the blood, which is then carried to the heart and other organs; thus alleviating fatigue; aids in bringing nourishment to cells; strengthens the capillary walls and prevents the red blood cells from destructive poisons; prevents and dissolves blood clots; and has also been used in helping prevent sterility, muscular dystrophy, calcium deposits in blood walls, and heart conditions.

Vitamin K is a group of substances of which the primary activity that makes the vitamin essential in human metabolism is its involvement in the blood-clotting system through synthesis of prothrombin and other clotting factors. Vitamin K contributes to biosynthesis of bone protein, and is necessary for the formation of prothrombinogen and other blood clotting factors in the liver. During clotting, circulating prothrombin is required for the production of thrombin. In turn, thrombin converts fibrinogen to fibrin, the network of which constitutes the clot. It is obvious from this description that interference with formation of prothrombin will reduce the clotting tendency of blood. In a deficiency of the vitamin, a condition of hypoprothrombinemia occurs, and blood-clotting time may be greatly, or even indefinitely, prolonged. Internal or external hemorrhages may ensue either spontaneously or following injury or surgery.

Water-soluble vitamins. Except for ascorbic acid, all of the vitamins in this category belong the B-group of vitamins. Some still retain their original individual designations, such as B-1, B-6, and B-12, whereas comparable names for other vitamins have become obsolete.

Vitamin C, or ascorbic acid, is known to be essential for the formation of intercellular collagen. Symptoms of scurvy, due to vitamin C deficiency, include bleeding gums, easy bruising and a tendency toward bone fractures. All these symptoms are a result of the requirement for vitamin C in the development of the ground substance between our cells. This ground substance, primarily collagen, is the cement that gives our tissues form and substance. Collagens are principal components of tendons, ligaments, skin, bone, teeth, cartilage, heart valves, intervertebral discs, cornea, eye lens, in addition to the ground substance between cells. Some collagen forms in the absence of ascorbic acid, but the fibers are abnormal, resulting in skin lesions and blood vessel fragility, characteristics of scurvy. In scorbutic tissues the amorphous ground substance and the fibroblasts in the area between the cells appear normal but without the matrix of collagen fibers. These bundles of collagenous material appear within a few hours after administration of ascorbic acid. This points to the relationship of the vitamin in maintenance of tooth structures, matrix of bone, and the walls of capillaries. Vitamin C is essential for the healing of bone fractures. Such fractures heal slowly in a patient deficient in vitamin C. This is true also of wound healing.

Vitamin C is also an antioxidant. Oxygen is a highly reactive element, and the process of reacting with certain chemicals is termed oxidation. Oxidation is not always bad. For example, the iron in hemoglobin oxidizes to carry oxygen to all the cells of the body. But much oxidation is damaging, accelerating aging and contributing to tissue and organ damage. Oxidation is also a contributor to heart disease (low density lipoprotein (LDL) oxidation has been linked to atherosclerosis) and cancer. As research continues, the more free-radical damage appears to contribute to chronic conditions and the more antioxidant nutrition supplementation is realized to be is essential. Vitamin C is the most effective water-soluble antioxidant in human plasma. Vitamin C is also a requirement for the proper functioning of the immune system. It is involved in white blood cell production, T-cells, and macrophages.

Biotin functions in synthesis and breakdown of fatty acids and amino acids through aiding the addition and removal of carbon dioxide to or from active compounds. It similarly acts in catalyzing deamination of amino acids and in oleic acid synthesis. Biotin is also an essential component of enzymes and aids in the utilization of protein and certain other vitamins, such as folic acid, pantothenic acid, and vitamin B-12.

Folic acid or folacin is one of the important hematopoietic agents necessary for proper regeneration of blood-forming elements and their functioning. Folic acid is also involved as a coenzyme in intermediary metabolic reactions in which one-carbon units are transferred. These reactions are important in interconversions of various amino acids and in purine and pyrimidine synthesis. The biosynthesis of purines and pyrimidines is ultimately linked with that of nucleotides and ribo- and deoxyribo-nucleic acids, functional elements in all cells.

Niacin (nicotinic acid) and niacinamide (nicotinamide) have identical properties as vitamins. In the body niacin is converted to niacinamide, which is an essential constituent of coenzymes I and II that occur in a wide variety of enzyme systems involved in anaerobic oxidation of carbohydrates. The coenzyme serves as a hydrogen acceptor in the oxidation of the substrate. These enzymes are present in all living cells and take part in many reactions of biological oxidation. Nicotinamide-adenine dinucleotide (NAD) and nicotinamide-adenine dinucleotide phosphate (NADP) are coenzymes synthesized in the body that take part in the metabolism of all living cells. Since they are of such widespread and vital importance, it is not difficult to see why serious disturbance of metabolic processes occurs when the supply of niacin to the cell is interrupted. Niacin is readily absorbed from the intestinal tract, and large doses may be given orally or parenterally with equal effect. Further, niacin improves circulation and reduces the cholesterol level in the blood; maintains the nervous system; helps metabolize protein, sugar & fat; reduces high blood pressure; increases energy through proper utilization of food; prevents pellagra; and helps maintain a healthy skin, tongue, and digestive system.

Pantothenic acid is of the highest biological importance because of its incorporation into Coenzyme A (CoA), which is involved in many vital enzymatic reactions transferring a two-carbon compound (the acetyl group) in intermediary metabolism. It is involved in the release of energy from carbohydrate and protein, in the degradation and metabolism of fatty acids, and in the synthesis of such compounds as sterols and steroid hormones, porphyrins, and acetylcholine. Pantothenic acid also participates in the utilization of vitamins; improves the body's resistance to stress; helps in cell building & the development of the central nervous system; helps the adrenal glands, and fights infections by participating in building of antibodies.

Pyridoxine (vitamin B-6) does not denote a single substance, but is rather a collective term for a group of naturally occurring pyridines that are metabolically and functionally interrelated: namely, pyridoxine, pyridoxal, and pyridoxamine. They are interconvertible in vivo in their phosphorylated form. Vitamin B-6 in the form of pyridoxal phosphate or pyridoxamine phosphate functions in carbohydrate, fat, and protein metabolism. Its major functions are most closely related to protein and amino acid metabolism. The vitamin is a part of the molecular configuration of many enzymes (a coenzyme), notably glycogen phosphorylase, various transaminases, decarboxylases, and deaminases. The latter three are essential for the anabolism and catabolism of proteins. Pyridoxine is also aids in fat and carbohydrate metabolism; aids in the formation of antibodies; maintains the central nervous system; aids in the removal of excess fluid of premenstrual women; promotes healthy skin; reduces muscle spasms, leg cramps, hand numbness, nausea and stiffness of hands; and helps maintain a proper balance of sodium and phosphorous in the body.

Riboflavin is another B vitamin, which plays its physiological role as the prosthetic group of a number of enzyme systems that are involved in the oxidation of carbohydrates and amino acids. It functions in combination with a specific protein either as a mononucleotide containing phosphoric acid (FMN), or as a dinucleotide combined through phosphoric acid with adenine (FAD). The specificity of each of the enzymes is determined by the protein in the complex. By a process of oxidation-reduction, riboflavin in the system either gains or loses hydrogen. The substrate, either carbohydrate or amino acid, may be oxidized by a removal of hydrogen. The first hydrogen acceptor in the chain of events is NAD or NADP, the di- or tri-nucleotide containing nicotinic acid and adenine. The oxidized riboflavin system then serves as hydrogen acceptor for the coenzyme system and in turn is oxidized by the cytochrome system. The hydrogen is finally passed on to the oxygen to complete the oxidative cycle. A number of flavoprotein enzymes have been identified, each of which is specific for a given substrate. Riboflavin also aids in the formation of antibodies and red blood cells; maintains cell respiration; necessary for the maintenance of good vision, skin, nails and hair; alleviates eye fatigue; and promotes general health.

Thiamine or thiamin is a generic term applied to all substances possessing vitamin B-1 activity, regardless of the anion attached to the molecule. The cationic portion of the molecule is made up of a substituted pyrimidine ring connected by a methylene bridge to the nitrogen of a substituted thiazole ring. In a phosphorylated form, thiamine serves as the prosthetic group of enzyme systems that are concerned with the decarboxylation of α-ketoacids. Some decarboxylation reactions are reversible, so that synthesis (condensation) may be achieved. Thus, thiamine is also important to the biosynthesis of keto-acids. It is involved in transketolase reactions. Thiamine is readily absorbed in aqueous solution from both the small and large intestine, and is then carried to the liver by the portal circulation. In the liver, as well as in all living cells, it normally combines with phosphate to form cocarboxylase. It may be stored in the liver in this form or it may combine further with manganese and specific proteins to become active enzymes known as carboxylases. Thiamine also plays a key role in the body's metabolic cycle for generating energy; aids in the digestion of carbohydrates; is essential for the normal functioning of the nervous system, muscles & heart; stabilizes the appetite; and promotes growth & good muscle tone.

Vitamin B-12 or cyanocobalamin is essential for the functioning of all cells, but particularly for cells of the bone marrow, the nervous system, and the gastrointestinal tract. It appears to facilitate reduction reactions and participate in the transfer of methyl groups. Its chief importance seems to be, together with folic acid, in the anabolism of DNA in all cells. It is a requisite for normal blood formation, and certain macrocystic anemias respond to its administration. Vitamin B-12 is also necessary for carbohydrate, fat, and protein metabolism; maintains a healthy nervous system; promotes growth in children; increases energy; and is needed for calcium absorption.

Preferred formulations and ranges of these ingredients, per ration, are:

| Vitamins | Ranges in Parts by Weight[1] or International Units (IU) | |
|---|---|---|
| | Broad | Preferred |
| A | 1,000–20,000 IU | 2,000–15,000 IU |
| D | 50–1,000 IU | 100–800 IU |
| E | 200–800 IU | 250–700 IU |
| K | $20-400 \times 10^{-6}$ | $20-300 \times 10^{-6}$ |
| C | $500-3,000 \times 10^{-3}$ | $500-3,000 \times 10^{-3}$ |
| Thiamine (B-1) | $1-100 \times 10^{-3}$ | $1-50 \times 10^{-3}$ |
| Riboflavin (B-2) | $1-100 \times 10^{-3}$ | $1-50 \times 10^{-3}$ |
| Niacin (B-3) | $0.5-50 \times 10^{-3}$ | $10-50 \times 10^{-3}$ |
| Pantothenic Acid (B-5) | $2-200 \times 10^{-3}$ | $2-100 \times 10^{-3}$ |
| Pyridoxine (B-6) | $1-100 \times 10^{-3}$ | $1-50 \times 10^{-3}$ |
| Folate | $50-5,000 \times 10^{-6}$ | $100-1,000 \times 10^{-6}$ |
| B-12 | $2-200 \times 10^{-6}$ | $5-50 \times 10^{-6}$ |
| Biotin | $50-5,000 \times 10^{-6}$ | $100-1,000 \times 10^{-6}$ |

[1]It is to be understood that any ranges expressed in the table without units are in reference to parts by weight Minerals Minerals serve a wide variety of essential physiological functions ranging from structural components of body tissues to essential components of many enzymes and other biological important molecules. Minerals are classified as micronutrients or trace elements on the basis of the amount present in the body. The seven micronutrients (calcium, potassium, sodium, magnesium, phosphorus, sulphur, and chloride) are present in the body in quantities of more than five grams. Trace elements, which include boron, copper, iron, manganese, selenium, and zinc are found in the body in quantities of less than five grams.

Micronutrient Minerals. Calcium is the mineral element believed to be most deficient in the diet in the United States. Calcium intakes in excess of 300 mg per day are difficult to achieve in the absence of milk and dairy products in the diet. This is far below the recommended dietary allowance (RDA) for calcium (1000 mg per day for some adults and children ages one to ten (more for older adults), 1200 mg per day for adolescents and pregnant and lactating women, which equates to about four glasses of milk per day). In fact, it has been reported that the mean daily calcium intake for females over age 12 does not exceed 85 percent of the RDA. In addition, during the years of peak bone mass development (18 to 30), more than 66 percent of all U.S. women fail to consume the recommended amounts of calcium on any given day. After age 35, this percentage increases to over 75 percent.

Although the general public is not fully aware of the consequences of inadequate mineral intake over prolonged periods of time, there is considerable scientific evidence that low calcium intake is one of several contributing factors leading to osteoporosis. In addition, the dietary ratio of calcium to phosphorous (Ca:P) relates directly to bone health. A Ca to P ratio of 1:1 to 2:1 is recommended to enhance the viability and health of bone marrow in humans. Such ratios are difficult to achieve absent an adequate dietary supply of milk and dairy products, or an adequate supply of calcium and other minerals for the lactose-intolerant segment of the population.

Magnesium is the second most plentiful cation of the intracellular fluids. It is essential for the activity of many enzyme systems and plays an important role with regard to neurochemical transmission and muscular excitability. Deficits are accompanied by a variety of structural and functional disturbances. The average 70-kg adult has about 2000 mEq of magnesium in his body. About 50% of this magnesium is found in bone, 45% exists as an intracellular cation, and 5% is in the extracellular fluid. About 30% of the magnesium in the skeleton represents an exchangeable pool present either within the hydration shell or on the crystal surface. Mobilization of the cation from this pool in bone is fairly rapid in children, but not in adults. The larger fraction of magnesium in bone is apparently an integral part of bone crystal.

The average adult in the United States ingests about 20 to 40 mEq of magnesium per day in an ordinary diet, and of this about one third is absorbed from the gastrointestinal tract. The evidence suggests that the bulk of the absorption occurs in the upper small bowel. Absorption is by means of an active process apparently closely related to the transport system for calcium. Ingestion of low amounts of magnesium results in increased absorption of calcium and vice versa.

Magnesium is a cofactor in all enzymes involved in phosphate transfer reactions that utilize adenosine triphosphate (ATP) and other nucleotide triphosphates as substrates. Various phosphatases and pyrophosphatases also represent enzymes from an enormous list that are influenced by this metallic ion.

Magnesium plays a vital role in the reversible association of intracellular particles and in the binding of macromolecules to subcellular organelles. For example, the binding of messenger RNA (mRNA) to ribosomes is magnesium dependent, as is the functional integrity of ribosomal subunits. Certain of the effects of magnesium on the nervous system are similar to those of calcium. An increased concentration of magnesium in the extracellular fluid causes depression of the central nervous system (CNS). Hypomagnesemia causes increased CNS irritability, disorientation, and convulsions. Magnesium also has a direct depressant effect on skeletal muscle. Abnormally low concentrations of magnesium in the extracellular fluid result in increased acetylcholine release and increased muscle excitability that can produce tetany.

Trace Elements. Boron is required by the body in trace amounts for proper metabolism of calcium, magnesium, and phosphorus. Boron helps brain function, healthy bones, and can increase alertness. Boron is also useful for people who want to build muscle. Boron is known to help prevent postmenopausal osteoporosis. Further, a relationship has been shown between a lack of boron in the diet and the chances of developing arthritis. R. E. Newnham, 46 Journal of Applied Nutrition (1994).

Chromium is an important trace element wherein the lack of sufficient chromium in the diet leads to impairment of glucose utilization, however, disturbances in protein and lipid metabolism have also been observed. Impaired glucose utilization occurs in many middle-aged and elderly human beings. In experimental studies, significant numbers of such persons have shown improvement in their glucose utilization after treatment with chromium. Chromium is transported by transferrin in the plasma and competes with iron for binding sites. Chromium as a dietary supplement may produce benefits due to its enhancement of glucose utilization and its possible facilitating the binding of insulin to insulin receptors, which increases its effects on carbohydrate and lipid metabolism. Chromium as a supplement may produce benefits in atherosclerosis, diabetes, rheumatism, and weight control.

Copper is another important trace element in the diet. The most common defect observed in copper-deficient animals is anemia. Other abnormalities include growth depression, skeletal defects, demyelination and degeneration of the nervous system, ataxia, defects in pigmentation and structure of hair or wool, reproductive failure and cardiovascular lesions, including dissecting aneurysms. Several copper-containing metalloproteins have been isolated, including tyrosinase, ascorbic acid oxidase, laccase, cytochrome oxidase, uricase, monoamine oxidase, δ-aminolevulinic acid hydrydase, and dopamine-β-hydroxylase. Copper functions in the absorption and utilization of iron, electron transport, connective tissue metabolism, phospholipid formation, purine metabolism, and development of the nervous system. Ferroxidase I (ceruloplasmin), a copper-containing enzyme, effects the oxidation of Fe(II) to Fe(III), a required step for mobilization of stored iron. A copper-containing enzyme is thought to be responsible for the oxidative deamination of the epsilon amino group of lysine to produce desmosine and isodesmosine, the cross-links of elastin. In copper-deficient animals the arterial elastin is weaker and dissecting aneurisms may occur.

Iodine is important for the production of thyroid hormones, which regulate cellular oxidation. The iodine-deficiency disease is goiter. In iodine-deficient young, growth is depressed and sexual development is delayed, the skin and hair are typically rough, and the hair becomes thin. Cretinism, feeble-mindedness, and deaf-mutism occur in a severe deficiency. There is reproductive failure in females and decreased fertility in males that lack sufficient iodine in the diet.

Iron is an essential component of several important metalloproteins. These include hemoglobin, myoglobin, and many oxidation-reduction enzymes. In iron deficiency, there may be reduced concentrations of some of the iron-containing enzymes, such as cytochrome c in liver, kidney, and skeletal muscle, and succinic dehydrogenase in the kidney and heart.

Manganese plays a role in the synthesis of GAGs, collagen, and glycoproteins, which are important constituents of cartilage and bone. Manganese is required for enzyme activity of glycosyltransferases. This family of enzymes is responsible for linking sugars together into GAGs, adding sugars to other glycoproteins, adding sulfate to aminosugars, converting sugars to other modified sugars, and adding sugars to lipids. These functions are manifested as GAG synthesis (hyaluronic acid, chondroitin sulfate, keratin sulfate, heparin sulfate, and dermatin sulfate, among others), collagen synthesis, and function of many other glycoproteins and glycolipids. GAGs and collagen are chief structural elements for all connective tissues. Their synthesis is essential for proper maintenance and repair of connective tissues.

Manganese deficiencies in humans and animals lead to abnormal bone growth, swollen and enlarged joints, and slipped tendons. In humans, manganese deficiencies are associated with bone loss, arthritis, and impaired glucose utilization. Levels of all GAGs are decreased in connective tissues during manganese deficiencies, with chondroitin sulfates being most depleted. Manganese-deficient organisms quickly normalize GAG and collagen synthesis when manganese is provided.

Manganese is also required for activity of manganese superoxide dismutase (MnSOD), which is present only in mitochondria. Manganese deficiency decreases the activity of MnSOD and may lead to mitochondrial dysfunction, manifested as decreased cellular functions. Manganese is required for the conversion of mevalonic acid to squalene. Pyruvate carboxylase is a manganese metalloenzyme, repressible by insulin, important in the citric acid cycle for the oxidation of carbohydrates, lipids, and proteins, as well as in the synthesis of glucose and lipids.

Molybdenum is an essential mineral found in highest concentrations in the liver, kidneys, skin, and bones. This mineral is required by the body to properly metabolize nitrogen. It is also a vital component of the enzyme xanthine oxidase, which is required to convert purines to uric acid, a normal byproduct of metabolism. Molybdenum also supports the body's storage of iron and other cellular functions such as growth. A deficiency of molybdenum is associated with mouth and gum disorders and cancer. A diet high in refined and processed foods can lead to a deficiency of molybdenum, resulting in anemia, loss of appetite and weight, and stunted growth in animals. While these deficiencies have not been observed directly in humans, it is known that a molybdenum deficiency can lead to impotence in older males.

Selenium is an essential trace element that functions as a component of enzymes involved in protection against antioxidants and thyroid hormone metabolism. In several intra- and extra-cellular glutathione peroxidases and iodothyronine 5'-deiodinases, selenium is located at the active centers as the selenoamino acid, selenocysteine (SeCYS). At least two other proteins of unknown function also contain SeCYS. Although SeCYS is an important dietary form, it is not directly incorporated into these specific selenium-proteins; instead, a co-translational process yields tRNA-bound SeCYS. In contrast, selenium as seleno-methionine is incorporated non-specifically into many proteins, as it competes with methionine in general protein synthesis. Therefore, tissues often contain both specific, as well as the nonspecific, selenium-containing proteins when both SeCYS and selenomethionine are consumed, as found in many foods. Selenium is a major antioxidant nutrient and is involved in protecting cell membranes and preventing free radical generation, thereby decreasing the risk of cancer and disease of the heart and blood vessels. Medical surveys show that increased selenium intake decreases the risk of breast, colon, lung and prostate cancer. Selenium also preserves tissue elasticity; slows down the aging and hardening of tissues through oxidation; and helps in the treatment and prevention of dandruff. Recent research has shown antitumorigenic effects of high levels of selenium in the diets of several animal models.

Vanadium is an essential nutrient beneficial for thyroid hormone metabolism. The daily requirement necessary to prevent a deficiency is about 10 to 20 micrograms a day. Vanadium deficiency can lead to slow growth, defective bones, and altered lipid metabolism. Vanadium exerts an insulin-like effect in some respects, and there has been a considerable amount of research on vanadium and diabetes. In insulin dependent diabetics, vanadium has been found to reduce the amount of insulin required to manage the disease, and in non-insulin dependent diabetics, vanadium has been known to control the condition altogether. Research has shown that supplementation with vanadium leads to an increase in glucose transport into cells, which suggests that vanadium supplementation of the diet improves glucose metabolism and may aid in preventing diabetes.

Zinc is known to occur in many important metalloenzymes. These include carbonic anhydrase, carboxypeptidases A and B, alcohol dehydrogenase, glutamic dehydrogenase, D-glyceraldehyde-3-phosphate dehydrogenase, lactic dehydrogenase, malic dehydrogenase, alkaline phosphatase, and aldolase. Impaired synthesis of nucleic acids and proteins has been observed in zinc deficiency. There is also evidence that zinc may be involved in the secretion of insulin and in the function of the hormone.

Preferred formulations and ranges of these ingredients, per ration, are:

| Minerals | Ranges in Parts by Weight | |
|---|---|---|
| | Broad | Preferred |
| Calcium | $500–2,000 \times 10^{-3}$ | $500–1,500 \times 10^{-3}$ |
| Magnesium | $50–1,000 \times 10^{-3}$ | $100–800 \times 10^{-3}$ |
| Chromium | $10–500 \times 10^{-6}$ | $10–300 \times 10^{-6}$ |
| Copper | $1–10 \times 10^{-3}$ | $1–5 \times 10^{-3}$ |
| Iodine | $10–500 \times 10^{-6}$ | $10–300 \times 10^{-6}$ |
| Iron | $1–20 \times 10^{-3}$ | $2–10 \times 10^{-3}$ |
| Manganese | $1–100 \times 10^{-3}$ | $1–50 \times 10^{-3}$ |
| Molybdenum | $5–500 \times 10^{-6}$ | $10–200 \times 10^{-6}$ |
| Selenium | $20–1,000 \times 10^{-6}$ | $20–500 \times 10^{-6}$ |
| Zinc | $2–200 \times 10^{-3}$ | $5–100 \times 10^{-3}$ |
| Boron | $0.1–10 \times 10^{-3}$ | $0.5–5 \times 10^{-3}$ |
| Vanadium | $1–100 \times 10^{-6}$ | $1–50 \times 10^{-6}$ |

According to the present invention, minerals can be provided as inorganic compounds, such as chlorides, sulfates, and the like. In addition, some minerals can be provided in more bioavailable forms, such as amino acid chelates, which are well known in the art. U.S. Pat. No. 5,292,538. Examples of minerals that can be provided as amino acid chelates include calcium, magnesium, manganese, zinc, iron, boron, copper, molybdenum, and chromium.

Carotenoids

Carotenoids are a family of hundreds of plant pigments found in fruits and vegetables that are red, orange, and deep yellow in color, and also in some dark green leafy vegetables. See USDA-NCC Carotenoid Database for U.S. Foods (1998). Carotenoids are the precursors of most of the vitamin A found in animals. At least 10 different carotenoids exhibit provitamin A activity, including α- and β-carotenes and cryptoxanthin. As precursors of vitamin A, carotenoids exhibit an effect on vision, but carotenoids are known to have other beneficial effects in the diet, as well. For example, carotenoids are also known for their antioxidant activity in helping protect the body from free radical damage.

Volumes of research reveal that two carotenoids—lutein and zeaxanthin—are found in great concentrations in the macula of the eye. This research also indicates that maintaining high levels of these two carotenoids, especially lutein, may help diminish the effects of age-related macular degeneration, the leading cause of blindness in those over 65 years of age. Lutein acts as an antioxidant, protecting cells against the damaging effects of free radicals. As with the other carotenoids, lutein is not made in the body and, therefore, must be obtained from food or dietary supplements.

At one time researchers believed all antioxidants served the same purpose. Now there is growing evidence that individual antioxidants may be used by the body for specific purposes. Researchers believe that lutein is deposited into areas of the body most prone to free radical damage. One major example is the macula, a tiny portion of the retina. Research indicates that because of its antioxidant properties, lutein consumption may play a role in maintaining the health of the eyes, heart and skin as well as the breasts and cervix in women. In addition, scientists are studying lutein's possible role in age-related macular degeneration, cataracts, heart disease, and immune system health. Studies have also shown that lutein is associated with a reduction in lung, breast, and cervical cancer. In the vascular system, lutein is found in high-density lipoprotein ("HDL") or "good" cholesterol and may prevent low-density lipoprotein ("LDL") or "bad" cholesterol from oxidizing, which sets the cascade for heart disease.

Besides being a precursor of vitamin A, β-carotene is thought to be effective in helping to protect against some diseases, such as cancer, heart disease, and stroke.

Lycopene is an open-chain unsaturated carotenoid that imparts red color to tomatoes, guava, rosehip, watermelon, and pink grapefruit. Lycopene is a proven anti-oxidant that may lower the risk of certain diseases including cancer and heart disease. In the body, lycopene is deposited in the liver, lungs, prostate gland, colon, and skin. Its concentration in body tissues tends to be higher than all other carotenoids. Epidemiological studies have shown that high intake of lycopene-containing vegetables is inversely associated with the incidence of certain types of cancer. For example, habitual intake of tomato products has been found to decrease the risk of cancer of the digestive tract among Italians. In one six-year study by Harvard Medical School and Harvard School of Public Health, the diets of more than 47,000 men were studied. Of 46 fruits and vegetables evaluated, only the tomato products (which contain large quantities of lycopene) showed a measurable relationship to reduce prostate cancer risk. As consumption of tomato products increased, levels of lycopene in the blood increased, and the risk for prostate cancer decreased. Ongoing research suggests that lycopene can reduce the risk of macular degenerative disease, serum lipid oxidation, and cancers of the lung, bladder, cervix and skin. Studies are underway to investigate other potential benefits of lycopene including lycopene's potential in the fight against cancers of the digestive tract, breast, and prostate. W. Stahl & H. Sies, Lycopene: a biologically important carotenoid for humans? 336 Arch. Biochem. Biophys. 1–9 (1996); H. Gerster, The potential role of lycopene for human health, 16 J. Amer. Coll. Nutr. 109–126 (1997).

Preferred formulations and ranges of these ingredients, per ration, are:

| Carotenoids | Ranges in Parts by Weight | |
|---|---|---|
| | Broad | Preferred |
| α-Carotene | $20–500 \times 10^{-6}$ | $20–400 \times 10^{-6}$ |
| β-Carotene | $1–20 \times 10^{-3}$ | $1–10 \times 10^{-3}$ |
| Cryptoxanthin | $5–200 \times 10^{-3}$ | $5–100 \times 10^{-3}$ |
| Lutein | $5–50 \times 10^{-3}$ | $5–20 \times 10^{-3}$ |
| Lycopene | $0.5–10 \times 10^{-3}$ | $1–10 \times 10^{-3}$ |
| Zeaxanthin | $50–1,000 \times 10^{-6}$ | $200–800 \times 10^{-6}$ |

Flavonoids

Flavonoids (also called bioflavonoids) are natural botanical pigments that provide protection from free-radical damage, among other functions. Bioflavonoids provide protection from damaging free radicals and are believed to reduce the risk of cancer and heart disease, decrease allergy and arthritis symptoms, promote vitamin C activity, improve the strength of blood vessels, block the progression of cataracts and macular degeneration, treat menopausal hot flashes, and other ailments. Flavonoids occur in most fruits and vegetables. It is believed that flavonoids act by inhibiting hormones, such as estrogen, that may trigger hormone-dependent malignancies like cancers of the breast, endometrium, ovary, and prostate. Studies show that quercetin, a flavonoid found in citrus fruits, can block the spread of cancer cells in the stomach. Flavonoids also stabilize mast cells, a type of immune cell that releases inflammatory compounds, like histamine, when facing foreign microorganisms. Histamine and other inflammatory substances are involved in allergic reactions. Mast cells are large cells present in connective tissue. Flavonoids fortify and repair connective tissue by promoting the synthesis of collagen. Collagen is a remarkably strong protein of the connective tissue that "glues" the cells together. Flavonoids are believed to benefit connective tissue and reduce inflammation.

Citrus bioflavonoids include isoquercetin, quercetin, hesperidin, rutin, naringen, naringenin, and limonene. Isoquercetin is a common flavonoid found in onions, apples, Arnica species, *Gossypium arboreum, Ginko biloba, Ricinus communis, Ocimum basilicum, Salix acutifolia*, and *Narcissus pseudonarcissus*. Rich dietary sources of quercetin are onions, apples, kale, sweet cherries, grapes, red cabbage, and green beans. Hesperidin is found in the rinds of oranges and lemons. It helps strengthen capillary walls in conjunction with vitamin C. Naringen is found in grapefruit and is responsible for most of grapefruit's bitter taste. Limonene, a flavonoid available in citrus fruits, promotes the production of enzymes that help destroy possible carcinogens (cancer-causing agents). Other bioflavonoids include: isoflavones, proanthocyanidins, anthocyanidins, ellagic acid, catechin, and tannin.

Isoquercetin shares the same aglycone with rutin and quercitrin: quercetin. It has been shown that quercetin-containing glycosides liberate quercetin in the intestinal tract. Therefore, it is justified to assume that all the pharmacological properties of quercetin are also shared by isoquercetin and rutin when administered orally. Recent investigation demonstrated a rapid absorption of isoquercetin and quercetin-glucosides by the sodium-dependent glucose transport pathway in the small intestine. Due to superior bioavailability, the health effects of isoquercetin are increased compared to other flavonoids. Isoquercetin is known to have anti-inflammatory activity without adverse effects on the gastrointestinal tract, such as those caused by non-steroidal anti-inflammatory drugs (NSAIDs). Isoquercetin further exhibits beneficial effects as an antioxidant, antihypertensive, anticarcinogenic, antimicrobial, and analgesic agent.

Quercetin is a bioflavonoid and a natural reverse transcriptase blocker commonly found in red apples and red onions. Quercetin has been shown to have antiviral activity against HIV, herpes simplex, and the respiratory syncytial virus. T. N. Kaul et al., Antiviral effects of flavonoids on human viruses, 15 J. Med. Virol. 71–79 (1985); R. Vrijsen et al., Antiviral activity of flavones and potentiation by ascorbate, 69 J. Gen. Virol. 1749–1751 (1988).

Grape seed extract is another source of bioflavonoids. Grape seed extract has been known to exhibit the following benefits: anti-inflammatory, antihistamine, antiallergenic, antioxidant (free radical scavenger), helps skin to remain young looking, improves circulation, promotes healing, restores collagen, strengthens weak blood vessels, and improves tissue elasticity. Some known applications include treatment of arthritis, allergies, hardening of arteries, ulcers, and skin problems.

Isoflavones are another group of phytochemicals that provide beneficial effects when provided as supplements to the diet. Isoflavones are also known as phytoestrogens (plant estrogens) and are one-hundredth to one-thousandth as potent as human estrogen. Although they are weak estrogens, researchers are finding that they can help offset the drop in estrogen that occurs naturally at menopause.

Isoflavones act like hormone replacement therapy (HRT), easing hot flashes. The main dietary sources of isoflavones are soybeans and soy foods, although some other legumes also contain small amounts. It's not clear how much soy actually is needed to get the most health benefit. Studies have shown that it may take as little as 20 grams of soy protein (about half an ounce), or about 2 cups of soy milk, or 2 ounces of tofu daily to help lessen symptoms.

Research also is underway to identify the roles isoflavones may play in protection from breast and prostate cancers. Isoflavones and soy protein also may prevent bone loss that leads to osteoporosis. Also, soy protein is being investigated for its lipid lowering effects. The most researched isoflavones are genistein, daidzein and glycitein. Data on the isoflavone content of foods is limited, however, the United States Department of Agriculture (USDA)—Iowa State University Isoflavone Database lists some common foods and their isoflavone content.

Preferred formulations and ranges of these ingredients, per ration, are:

| Bioflavonoids | Ranges in Parts by Weight | |
|---|---|---|
| | Broad | Preferred |
| Citrus Bioflavonoids | $5–500 \times 10^{-3}$ | $10–250 \times 10^{-3}$ |
| Grape Seed Extract | $5–200 \times 10^{-3}$ | $5–100 \times 10^{-3}$ |
| Quercetin | $5–200 \times 10^{-3}$ | $5–100 \times 10^{-3}$ |
| Rutin | $5–200 \times 10^{-3}$ | $5–100 \times 10^{-3}$ |
| Soybean Isoflavones | $10–500 \times 10^{-3}$ | $10–250 \times 10^{-3}$ |

Omega-3 Fatty Acids Sources

Flax, one of the world's most ancient cultivated plants, offers significant benefit in many diseases linked to modern living, including the three major killers of Americans: heart disease, cancer, and stroke. The optimal method of gaining the health promoting benefits of flax is by using flaxseed oil or some other suitable source of omega-3 fatty acids. Omega-3 fatty acids have been shown to lower cholesterol and triglycerides and help to prevent clots in arteries which may result in strokes, heart attacks, and thromboses. Flaxseed oil has been suggested for helping to prevent atherosclerosis, alleviating some cases of asthma, lowering elevated blood pressure in hypertension sufferers, improving the function of the liver, treating some cases of edema, alleviating some cases of alopecia areata, alleviating some symptoms of allergies, alleviating side-effects and inhibiting further development of many forms of cancer, improving the condition of persons afflicted with discoid lupus erythematosus (DLE), alleviating symptoms of diabetes mellitus (by lowering the amount of insulin required), increasing the body's production of energy and improving stamina, facilitating weight loss in persons afflicted with obesity, accelerating healing of bruises and sprains, helping in the treatment of dandruff and eczema, improving eyesight and color perception, strengthening nails, treating psoriasis, alleviating symptoms of rheumatoid arthritis, treating some cases of depression, improving mental function of elderly people, treating and often improving the symptoms of multiple sclerosis, improving the behavior of schizophrenics, alleviating some cases of pre-menstrual syndrome (PMS), and improving metabolism and absorption of calcium.

Preferred formulations and ranges of omega-3 fatty acids sources, per ration, are:

| Omega-3 Fatty Acids Sources | Ranges in Parts by Weight | |
|---|---|---|
| | Broad | Preferred |
| Flax Seed Oil | $50–2,000 \times 10^{-3}$ | $100–2,000 \times 10^{-3}$ |

Aminosugars and Glycosaminoglycans (Cartilage Protectors)

The connective tissues are constantly subjected to stresses and strains from mechanical forces that can result in afflictions, such as arthritis, joint inflammation, and stiffness. Such afflictions are especially acute in joints, such as the neck, back, arms, hips, knees, ankles, and feet. Indeed, connective tissue afflictions are quite common, presently affecting millions of Americans. Further, such afflictions can be not only painful, but can also be debilitating.

The connective tissues are naturally equipped to repair themselves by manufacturing and remodeling prodigious amounts of collagen and proteoglycans (the major components of connective tissues). This ongoing process is placed under stress when an injury occurs to connective tissues. In such cases, the production of connective tissue (along with collagen and proteoglycans) can double or triple over normal amounts, thereby increasing the demand for the building blocks of both collagens and proteoglycans. The building blocks for collagen are amino acids. Proteoglycans are large and complex macromolecules comprises mainly of long chains of modified sugars called glycosaminoglycans (GAGs) or mucopolysaccharides. Proteoglycans provide the framework for collagen to follow. They also hold water to give the connective tissues (especially cartilage) flexibility, resiliency, and resistance to compression. In the production of proteoglycans, the rate-limiting step is the conversion of glucose to glucosamine for the production of GAGs. Glucosamine, an aminosugar, is the key precursor to all the various modified sugars found in GAGs-glucosamine sulfate, galactosamine, N-acetylglucosamine, etc. Glucosamine also makes up 50% of hyaluronic acid, the backbone of proteoglycans, on which other GAGs, like chondroitin sulfates are added. The GAGs are then used to build proteoglycans and, eventually, connective tissue. Once glucosamine is formed, there is no turning away from the synthesis of GAGs and collagen.

The composition of the present invention preferably includes an aminosugar, such as glucosamine (preferably in a salt form) and a GAG, such as chondroitin (preferably in a salt form). The aminosugar, glucosamine, provides the primary substrate for both collagen and proteoglycan synthesis. In fact, glucosamine is the preferred substrate for proteoglycan synthesis, including chondroitin sulfates and hyaluronic acid. The glucosamine is, preferably, in a salt form so as to facilitate its delivery and uptake. The preferred salt forms are glucosamine hydrochloride and glucosamine sulfate. N-acetylglucosamine is another preferred form of glucosamine. It should be noted that, in the case of glucosamine sulfate, the sulfate may be available for later use in catalyzing the conversion of glucosamine to GAGs. The unsulfated form is desired for the production of hyaluronic acid.

Glucosamine has been shown to be rapidly and almost completely absorbed into humans after oral administration. A significant portion of the ingested glucosamine localizes to cartilage and joint tissues, where it remains for long periods of time. This indicates that oral administration of glucosamine reaches connective tissues, where glucosamine is incorporated into newly-synthesized connective tissue.

Chondroitin sulfate is a glycosaminoglycan that provides a further substrate for synthesis of proteoglycan. Once again, the provision of chondroitin in its salt, especially sulfate, form facilitates its delivery and uptake by humans. Also, the sulfate is available for sulfation of the GAGs.

Chondroitin sulfate not only provides additional organic sulfur for incorporation into cartilage, but it also has a synergistic effect with glucosamine, since its structure provides galactosamine, which is synthesized by a different pathway than glucosamine. Karzel et al., 5 Pharmacology 337–3435 (1971). In addition, chondroitin sulfate has been shown to have cardiovascular health benefits, Morrison et al., Coronary Hearth Disease and the Mucopolysaccharides 109–127 (1973), and also helps prevent degradation or breakdown of cartilage.

Preferred formulations and ranges of these ingredients, per ration, are:

| Cartilage Protectors | Ranges in Parts by Weight | |
|---|---|---|
| | Broad | Preferred |
| Glucosamine | $200–2,000 \times 10^{-3}$ | $200–1,500 \times 10^{-3}$ |
| Chondroitin | $50–1,500 \times 10^{-3}$ | $150–1,200 \times 10^{-3}$ |

Other Nutrients

Alpha-lipoic acid (technically known as DL-alpha lipoic acid) is a powerful antioxidant being researched for unique properties that may provide both preventive and therapeutic benefits in numerous conditions and diseases including diabetes, heart disease, and even possibly HIV infection. Lipoic acid and its reduced form, DHLA, show the ability to directly quench a variety of reactive oxygen species, inhibit reactive oxygen generators, and spare and regenerate other antioxidants. Lipoic acid not only protects the nervous system, but is also involved in regenerating nerves. It is also being studied in the treatment of Parkinson's disease and Alzheimer's disease. Lipoic acid is best known for its ability to help regenerate damaged liver tissue when nothing else will. Lipoic acid is marketed in Germany for treating diabetic neuropathy. It also has an essential role in mitochondrial dehydrogenase reactions.

Coenzyme Q10 is an essential electron and proton carrier that functions in the production of biochemical energy in aerobic organisms. Coenzyme Q10 is found in every cell in the body, thus its other name, ubiquinone (from the word ubiquitous and the coenzyme quinone). The structure of coenzyme Q10 consists of a quinone ring attached to an isoprene side chain. Because the body must have energy available to perform even the simplest operation, coenzyme Q10 is considered essential for the body's cells, tissues, and organs. Coenzyme Q10 also has antioxidant and membrane stabilizing properties that serve to prevent the cellular damage that results from normal metabolic processes. Even though the body has the ability to produce coenzyme Q10, deficiencies have been reported in a range of clinical conditions. Supplementation of the coenzyme helps guard against a possible deficiency. Aging is considered one reason for a deficiency, since the liver loses its ability to synthesize coenzyme Q10 as one gets older. Besides aging, poor eating habits, stress, and infection affect the body's ability to provide adequate amounts of coenzyme Q10. Known results of using coenzyme Q10 as an oral supplement are energy increase, improvement of heart function, prevention and cure of gum disease, a boost to the immune system, and possible life extension. AIDS is a primary target for research on coenzyme Q10 because of its immense benefits to the immune system. Further, coenzyme Q10 has also been reported to provide a salutary effect in the treatment of breast cancer.

Preferred formulations and ranges of these ingredients, per ration, are:

| Other Ingredients | Ranges in Parts by Weight | |
|---|---|---|
| | Broad | Preferred |
| α-Lipoic Acid | $5–500 \times 10^{-3}$ | $5–250 \times 10^{-3}$ |
| Coenzyme Q10 | $1–100 \times 10^{-3}$ | $1–50 \times 10^{-3}$ |

EXAMPLE

The following formulae represent specific embodiments of the invention. These embodiments can be prepared by blending together the stated dry raw materials in an agglomerator to result in a product having a uniform composition with the precise proportions of the components as indicated. More than one ingredient is oil-based, and such ingredients are preferably blended and distributed over the dry ingredients. If flax seed oil is to be added, said oil is mixed with the blended dry ingredients and oil-based ingredients, and the resulting mixture is a product having a uniform composition. The agglomerated material is then preferably placed in capsules according to methods well known in the art, such as is summarized in Remington's Pharmaceutical Sciences, in quantities of one ration per capsule. As a frame of reference, Formulation II, as set out below, is intended to be encapsulated in 7 "00" capsules, each containing about 1.0 to 1.3 g/ml. Other formulations can be encapsulated in any suitable number and size of capsules, in accordance with the knowledge of one of ordinary skill in the relevant art of capsule sizing and quantifying. Size "00" capsules have a capsule volume of about 0.95 ml. Other capsule sizes could be selected according to principles well known in the pharmaceutical arts. In the preferred embodiment, the composition comprises the following ingredients stated in amounts by weight or international units (IU):

| Ingredients | Formulation Number | | | | | | | |
|---|---|---|---|---|---|---|---|---|
| | I | II | III | IV | V | VI | VII | VIII |
| Vitamin A (IU) | 2000 | 10,000 | | 8000 | | 5000 | | |
| Vitamin D (IU) | 120 | 400 | | 500 | | 600 | | |
| Vitamin E (IU) | 250 | 400 | 600 | 300 | 550 | 700 | 400 | 500 |
| Vitamin K (µg) | 300 | 80 | | 20 | | 50 | | |
| Vitamin C (mg) | 500 | 1500 | 2000 | 1000 | 1500 | 750 | 1200 | 800 |
| Thiamine (mg) | 50 | 10 | | | 5 | 1 | | |
| Riboflavin (mg) | 50 | 10 | | | 5 | 1 | | |
| Niacin (mg) | 50 | 40 | | | | 10 | 20 | |
| Pyridoxine (mg) | 1 | 10 | | | | 40 | 30 | |
| Folate (µg) | 100 | 600 | | | | 900 | 200 | |

-continued

| Ingredients | I | II | III | IV | V | VI | VII | VIII |
|---|---|---|---|---|---|---|---|---|
| Vitamin B-12 (μg) | 5 | 25 | | | 50 | 30 | | |
| Biotin (μg) | 100 | 400 | | | | 600 | 500 | |
| Pantothenic Acid (mg) | 100 | 20 | | | 5 | 30 | | |
| Ca (mg) | 1500 | 1000 | 800 | 500 | 1200 | 1000 | 1300 | 800 |
| Mg (mg) | 100 | 400 | | 600 | | 800 | | |
| Cr (μg) | 300 | 150 | | | | 10 | | 200 |
| Cu (mg) | 1 | 3 | | | | 5 | | 1 |
| I (μg) | 10 | 150 | | | | 300 | | 50 |
| Fe (mg) | 2 | 6 | | | | 10 | | 5 |
| Mn (mg) | 50 | 10 | | | | 1 | | 20 |
| Mo (μg) | 200 | 75 | | | | 10 | | 100 |
| Se (μg) | 20 | 200 | | | | 500 | | 100 |
| Zn (mg) | 5 | 20 | | | | 100 | | 50 |
| B (mg) | 2 | 1 | | | | 5 | | 0.5 |
| V (μg) | 20 | 10 | | | | 1 | | 50 |
| α-Carotene (μg) | 400 | 196 | | 20 | | | | 200 |
| β-Carotene (mg) | 1 | 6 | | 8 | | 10 | | |
| Cryptoxanthin (mg) | 100 | 49 | 20 | | 90 | | | |
| Lutein (mg) | 5 | 10 | | 20 | 10 | 15 | | |
| Lycopene (mg) | 1 | 2 | | 10 | 5 | | | |
| Zeaxanthin (μg) | 800 | 539 | 200 | | | 600 | | |
| Citrus Bioflavonoids (mg) | 250 | 50 | | | | 10 | 100 | |
| Grape Seed Extract (mg) | 5 | 25 | | | | 100 | 50 | |
| Quercetin (mg) | 100 | 25 | | | | 100 | 50 | |
| Rutin (mg) | 5 | 25 | | | | 100 | 75 | |
| Soybean Isoflavones (mg) | 100 | 62 | | | | 250 | 10 | |
| Flax Seed Oil (mg) | 1000 | 500 | | | | 100 | 2000 | |
| Glucosamine (mg) | 500 | 750 | | | | 1000 | 200 | |
| Chondroitin (mg) | 1000 | 600 | | | | 150 | 1200 | |
| α-Lipoic Acid (mg) | 25 | 50 | | | 100 | | 5 | |
| Coenzyme Q10 (mg) | 25 | 10 | | | | 5 | 50 | |

With respect to the present invention and all ingredients and ranges of ingredients thereof, it is to be understood that the preferred formulations, ranges of ingredients, and the ingredients list itself, will likely change over time as applicants perfect and refine the formulations. Applicants intend to conduct regular scientific review, and reformulate the nutritional supplement accordingly. It is further to be understood that the nutritional supplement of the present invention is a multi-system, multi-nutrient, comprehensive supplement that simultaneously addresses the many systems of the human body as discussed herein. Accordingly, unlike many other nutritional supplements, the nutritional supplement of the present invention is not limited in its application simply to one or two systems, such as cartilage and connective tissue, but is in reality a treatment of all described systems.

Method for Supplementing a Person's Diet

According to the present invention, a method for supplementing a person's diet comprises providing amounts of vitamins, minerals, carotenoids, and other optional ingredients according to the age, body weight, and quality of diet of the person. It has been determined that a person whose age is 60 years or greater generally has a need for more supplemented nutrients than does a younger person. It has also been determined that persons of greater body weight generally have a need for more supplemented nutrients that persons of lower body weight. Therefore, three categories of body weight have been established, under 54.5 kg (<120 lbs.), 54.5 to 90.9 kg (120 to 200 lbs.), and over 90.9 kg (>200 lbs.). Further, it has been determined that persons eating a fair diet have more need for dietary supplementation than persons eating a good diet, who in turn have more need for dietary supplementation than persons eating an excellent diet. In accordance with these principles, the following table has been prepared for determining the number of rations of the present dietary supplement that should be taken on a daily basis according to the person's age, body weight, and quality of diet:

Daily Rations[1] of Dietary Supplement Blend Composition

| Age | Body weight | Excellent Diet | Good Diet | Fair Diet |
|---|---|---|---|---|
| <60 years | <54.5 kg (<120 lbs.) | 4 | 5 | 6 |
| | 54.5 to 90.9 kg (120 to 200 lbs.) | 5 | 6 | 7 |
| | >90.9 kg (>200 lbs.) | 6 | 7 | 8 |
| ≧60 years | <54.5 kg (<120 lbs.) | 5 | 6 | 7 |
| | 54.5 to 90.9 kg (120 to 200 lbs.) | 6 | 7 | 8 |
| | >90.9 kg (>200 lbs.) | 7 | 8 | 9 |

[1]Although the entire quantity of daily rations may be administered all at once, it is recommended that the rations instead be spread out in administrations of two to three times per day. For example, if the recommended quantity of daily rations is six, three administrations of two rations, spread throughout the day, is preferred.

Thus, for example, a person who is 65 years old, weighing between 120–200 pounds and eating a "good" diet, would consume seven (7) rations per day of the dietary supplement.

As another example, a 70-kg person who is 35 years of age and eating an "excellent" diet should consume five (5) rations per day of the dietary supplement.

The rations can be taken at any time of the day, but it is preferred that administrations of the daily rations be spread throughout the day among two to three administrations per day. For example, half the rations may be taken in the morning and half in the evening.

The preferred formulation is intended to be encapsulated in 7 "00" capsules, each containing about 1.0 to 1.3 g/ml, at a mass per capsule of approximately 1.0 to 1.3 g/ml (depending on several factors, such as percent volume filled within each capsule, use of flax seed oil or another source of omega-3 fatty acid). In accordance with the table above, the preferred daily dosage of the composition, in terms of mass-quantity of the composition per mass-quantity of body mass, ranges from 0.06 to 0.13 grams of the composition per kilogram of body mass.

It is also within the scope of the present invention to include, if desired, some substances that are of little or no nutritional value, but which are useful in the manufacture of the nutritional supplements. Such substances can include certain antioxidants and preservatives; coloring, flavoring, and diluting agents; emulsifying and suspending agents; solvents; and the like. As used herein, "diluents" are inert substances added to increase the bulk of the formulation to convenience in making the dosage form, such as capsulres. Commonly used diluents include calcium phosphate, calcium sulfate, lactose, kaolin, mannitol, sodium chloride, dry starch, powdered sugar, silica, and the like. As used herein, "binders" are agents used to impart cohesive qualities to the powdered material. Binders, or "granulators" as they are sometimes known, impart a cohesiveness to the formulation. as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like. As used herein, "lubricants" are materials that perform a number of functions in tablet manufacture, such as improving the rate of flow of the granulation and reducing interparticle friction. Commonly used lubricants include talc, magnesium stearate, calcium stearate, stearic acid, and hydrogenated vegetable oils. Preferred amounts of lubricants range from about 0.1% by weight to about 5% by weight As used herein, "coloring agents" are agents that give dosage forms a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye. In addition, other pigments, such as the white pigment, titanium dioxide, may be added.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for supplementing a person's diet comprising:
   (a) determining the person's age, body weight, and quality of diet, wherein an excellent diet comprises an average daily intake of at least 8 servings of vegetables or fruits, and at least a partial serving of a calcium source, wherein a good diet comprises an average daily intake of at least 5 servings of vegetables or fruits, and wherein a fair diet comprises an average daily intake of fewer than 5 servings of vegetables or fruits;
   (b) determining a number of daily rations of a dietary supplement blend composition to be administered to the person based on the person's age, body weight, and quality of diet from the table:

| Daily Rations of Dietary Supplement Blend Composition | | | | |
|---|---|---|---|---|
| Age | Body weight | Excellent Diet | Good Diet | Fair Diet |
| <60 years | <54.5 kg (<120 lbs.) | 4 | 5 | 6 |
| | 54.5 to 90.9 kg (120 to 200 lbs.) | 5 | 6 | 7 |
| | >90.9 kg (>200 lbs.) | 6 | 7 | 8 |
| ≧60 years | <54.5 kg (<120 lbs.) | 5 | 6 | 7 |
| | 54.5 to 90.9 kg (120 to 200 lbs.) | 6 | 7 | 8 |
| | >90.9 kg (>200 lbs.) | 7 | 8 | 9 | wherein the dietary supplement blend composition comprises:
   (1) about 500 to $5,000\times(10^{-3})$ parts by weight of vitamin C;
   (2) about 200 to 800 international units of vitamin E;
   (3) about 500 to $2,000\times(10^{-3})$ parts by weight of calcium; and
   (4) an effective amount of a carotenoid;
   (c) administering the number of daily rations of the dietary supplement blend composition to the person as determined from the person's age, body weight, and quality of diet.

2. The method of claim 1 wherein the effective amount of the carotenoid is about 10 to $300\times(10^{-3})$ parts by weight.

3. The method of claim 2 wherein the carotenoid is a member selected from the group consisting of α-carotene, β-carotene, cryptoxanthin, lutein, lycopene, zeaxanthin, and mixtures thereof.

4. The method of claim 3 wherein the dietary supplement blend composition further comprises about 30 to $1,500\times(10^{-3})$ parts by weight of a bioflavonoid selected from the group consisting of citrus bioflavonoids, grape seed extract, quercetin, rutin, soybean isoflavones, and mixtures thereof.

5. The method of claim 3 wherein the dietary supplement blend composition further comprises about 250 to $3,500\times(10^{-3})$ parts by weight of a cartilage protector selected from the group consisting of glucosamine, chondroitin, and mixtures thereof.

6. The method of claim 4 wherein the dietary supplement blend composition further comprises about 250 to $3,500\times(10^{-3})$ parts by weight of a cartilage protector selected from the group consisting of glucosamine, chondroitin, and mixtures thereof.

7. The method of claim 3 wherein the dietary supplement blend composition further comprises a fat soluble vitamin selected from the group consisting of about 1,000 to 20,000 international units of vitamin A; about 50 to 1,000 international units of vitamin D; about $20-400\times(10^{-6})$ parts by weight of vitamin K; and mixtures thereof.

8. The method of claim 6 wherein the dietary supplement blend composition further comprises a fat soluble vitamin selected from the group consisting of about 1,000 to 20,000 international units of vitamin A; about 50 to 1,000 international units of vitamin D; about 20–400×$(10^{-6})$ parts by weight of vitamin K; and mixtures thereof.

9. The method of claim 3 wherein the dietary supplement blend composition further comprises a water soluble vitamin selected from the group consisting of about 1 to 100×$(10^{-3})$ parts by weight of thiamine; about 1 to 100×$(10^{-3})$ parts by weight of riboflavin; about 0.5 to 50×$(10^{-3})$ parts by weight of niacin; about 1 to 100×$(10^{-3})$ parts by weight of pyridoxine; about 50 to 5,000×$(10^{-6})$ parts by weight of folic acid; about 2 to 200×$(10^{-6})$ parts by weight of vitamin B-12; about 50 to 5,000×$(10^{-6})$ parts by weight of biotin; about 2 to 200×$(10^{-3})$ parts by weight of pantothenic acid; and mixtures thereof.

10. The method of claim 8 wherein the dietary supplement blend composition further comprises a water soluble vitamin selected from the group consisting of about 1 to 100×$(10^{-3})$ parts by weight of thiamine; about 1 to 100×$(10^{-3})$ parts by weight of riboflavin; about 0.5 to 50×$(10^{-3})$ parts by weight of niacin; about 1 to 100×$(10^{-3})$ parts by weight of pyridoxine; about 50 to 5,000×$(10^{-6})$ parts by weight of folic acid; about 2 to 200×$(10^{-6})$ parts by weight of vitamin B-12; about 50 to 5,000×$(10^{-6})$ parts by weight of biotin; about 2 to 200×$(10^{-3})$ parts by weight of pantothenic acid; and mixtures thereof.

11. The method of claim 3 wherein the dietary supplement blend composition further comprises about 50 to 1,000×$(10^{-3})$ parts by weight of magnesium.

12. The method of claim 10 wherein the dietary supplement blend composition further comprises about 50 to 1,000×$(10^{-3})$ parts by weight of magnesium.

13. The method of claim 3 wherein the dietary supplement blend composition further comprises a trace element selected from the group consisting of about 10 to 500×$(10^{-6})$ parts by weight of chromium; about 1 to 10×$(10^{-3})$ parts by weight of copper; about 10 to 500×$(10^{-6})$ parts by weight of iodine; about 2 to 20×$(10^{-3})$ parts by weight of iron; about 1 to 100×$(10^{-3})$ parts by weight of manganese; about 5 to 500×$(10^{-6})$ parts by weight of molybdenum; about 20 to 1,000×$(10^{-6})$ parts by weight of selenium; about 2 to 200×$(10^{-3})$ parts by weight of zinc; about 0.1 to 10×$(10^{-3})$ parts by weight of boron; about 1 to 100×$(10^{-6})$ parts by weight of vanadium; and mixtures thereof.

14. The method of claim 12 wherein the dietary supplement blend composition further comprises a trace element selected from the group consisting of about 10 to 500×$(10^{-6})$ parts by weight of chromium; about 1 to 10×$(10^{-3})$ parts by weight of copper; about 10 to 500×$(10^{-6})$ parts by weight of iodine; about 2 to 20×$(10^{-3})$ parts by weight of iron; about 1 to 100×$(10^{-3})$ parts by weight of manganese; about 5 to 500×$(10^{-6})$ parts by weight of molybdenum; about 20 to 1,000×$(10^{-6})$ parts by weight of selenium; about 2 to 200×$(10^{-3})$ parts by weight of zinc; about 0.1 to 10×$(10^{-3})$ parts by weight of boron; about 1 to 100×$(10^{-6})$ parts by weight of vanadium; and mixtures thereof.

15. The method of claim 3 wherein the dietary supplement blend composition further comprises about 50 to 2,000×$(10^{-3})$ parts by weight of flax seed oil.

16. The method of claim 14 wherein the dietary supplement blend composition further comprises about 50 to 2,000×$(10^{-3})$ parts by weight of flax seed oil.

17. The method of claim 3 wherein the dietary supplement blend composition further comprises a member selected from the group consisting of about 5 to 500×$(10^{-3})$ parts by weight of α-lipoic acid; about 1 to 100×$(10^{-3})$ parts by weight of coenzyme Q10; and mixtures thereof.

18. The method of claim 16 wherein the dietary supplement blend composition further comprises a member selected from the group consisting of about 5 to 500×$(10^{-3})$ parts by weight of α-lipoic acid; about 1 to 100×$(10^{-3})$ parts by weight of coenzyme Q10; and mixtures thereof.

19. The method of claim 1, wherein said excellent diet further comprises an average daily intake of at least 1 serving of a calcium source, and at least 3 servings of unrefined grains, and wherein said good diet further comprises an average daily intake of at least 1 serving of unrefined grains.

\* \* \* \* \*